United States Patent [19]
Assenheimer et al.

[11] 4,011,288
[45] Mar. 8, 1977

[54] DISPOSABLE HUMIDIFIER ASSEMBLY

[75] Inventors: Robert Assenheimer, Boonton, N.J.; Michael O. Pekkarinen, Lincolnshire, Ill.

[73] Assignee: Baxter Travenol Laboratories, Inc., Deerfield, Ill.

[22] Filed: Mar. 14, 1975

[21] Appl. No.: 558,601

[52] U.S. Cl. .......................... 261/121 R; 128/187; 128/194; 222/83.5; 222/86; 261/DIG. 65
[51] Int. Cl.² ...................................... A61M 15/00
[58] Field of Search .............. 261/121 R, DIG. 65; 128/185, 186, 187, 188, 189, 190, 191, 192, 193, 194; 215/1 C; 222/85, 86, 83, 83.5

[56] References Cited

UNITED STATES PATENTS

| | | | |
|---|---|---|---|
| 2,709,577 | 5/1955 | Pohndorf et al. | 128/185 |
| 2,902,269 | 9/1959 | Eichelman | 128/186 |
| 3,208,639 | 9/1965 | Marwell et al. | 222/83 |
| 3,290,021 | 12/1966 | Blachly et al. | 261/91 |
| 3,652,015 | 3/1972 | Beall | 239/338 |
| 3,724,454 | 4/1973 | Brown | 128/194 |
| 3,771,721 | 11/1973 | Van Amerongen | 128/194 |
| 3,802,604 | 4/1974 | Morane et al. | 222/85 |
| 3,834,385 | 9/1974 | Pekkarinen | 128/194 |
| 3,846,518 | 11/1974 | McPhee | 128/194 |
| 3,852,385 | 12/1974 | Huggins | 128/188 |
| 3,861,386 | 1/1975 | Harris et al. | 128/194 |
| 3,938,520 | 2/1976 | Scislowcz et al. | 222/83 |

Primary Examiner—Tim R. Miles
Assistant Examiner—Gregory N. Clements
Attorney, Agent, or Firm—Paul C. Flattery; Garrettson Ellis

[57] ABSTRACT

A gas humidifier set is provided which includes a solution bottle containing a sterile water solution, a cap seal providing a sterile seal for the solution bottle, a connector assembly for penetrating the seal at the time of use and coupling the solution bottle to a gas supply and a covering cap for covering the connector assembly and maintaining it in sterile condition prior to use. The connector assembly includes gas inlet and outlet members. To use the device, the covering cap is removed and the connector assembly is turned thereby causing piercing of the cap seal and communication between the sterile water solution and the gas inlet and outlet members.

10 Claims, 7 Drawing Figures

DISPOSABLE HUMIDIFIER ASSEMBLY

BACKGROUND OF THE INVENTION

This invention relates to an improved system for humidifying medical gases that are administered to a patient, such as oxygen, air, helium or anesthesia gases.

The gas which is supplied to a hospital patient must be humidified because of the inherently low humidity of the gas exiting conventional gas tanks. The term "gas" as used herein is intended to include all types of gases, such as oxygen, air oxygen mixtures, helium and anesthesia gases. The term "water" as used herein is intended to include distilled water, tap water and other water-containing liquids, such as saline solution.

Disposable humidifier assemblies are in wide use in hospitals today. One type of disposable humidifier assembly depends upon an open water supply thereby providing an obvious risk of contamination. Another type of disposable humidifier assembly includes a plastic bottle containing sterile water. Although the top of the bottle is not sterile, a separate connector which couples the bottle to a gas supply must be inserted into the top of the bottle, thereby forcing a possibly contaminated portion of the bottle into an otherwise sterilized container portion.

It has been found desirable to provide a disposable humidifier assembly which utilizes a sterile solution and a connector assembly which can couple the sterile solution to a gas supply without placing the sterile solution in communication with possibly contaminated portions of either the bottle or the connector. Thus it is an object of the present invention to provide a disposable humidifier assembly which significantly avoids risk of contamination.

Another object of the present invention is to provide a disposable humidifier assembly that is relatively simple to manufacture and easy to use.

Other objects and advantages of the present invention will become apparent as the description proceeds.

BRIEF DESCRIPTION OF THE INVENTION

In accordance with the present invention, a novel gas humidifier set is provided. The gas humidifier set includes a solution bottle and a cap seal connected to the solution bottle to provide a sterile seal therefor. An airway tube is connected to the cap seal and extends to the lower portion of the bottle.

A connector assembly is provided for coupling the solution bottle to a gas supply. The connector assembly engages the opening wall portion and comprises a gas inlet member and a gas outlet member. The lower portion of the gas inlet member comprises a downwardly extending tube for piercing the cap seal when the outer cap of the connector assembly is moved in a predetermined direction.

Means are provided for coupling the upper portion of the gas inlet member to a gas supply and the gas outlet member is adapted for connection to a gas administration device. A covering cap is provided for covering the connector assembly and maintaining it in sterile condition prior to use.

The gas humidifier set of the illustrative embodiment is thus poised in position for easy use. When use is desired, the covering cap is simply separated from the bottle by turning a driving cap forwardly. The outer cap of the connector assembly is then merely turned and downwardly extending tubes will pierce the cap seal to automatically place the set in condition for use.

A more detailed explanation of the invention is provided in the following description and claims, and is illustrated in the accompanying drawings.

DETAILED DESCRIPTION OF THE ILLUSTRATIVE EMBODIMENT

Figure 1:
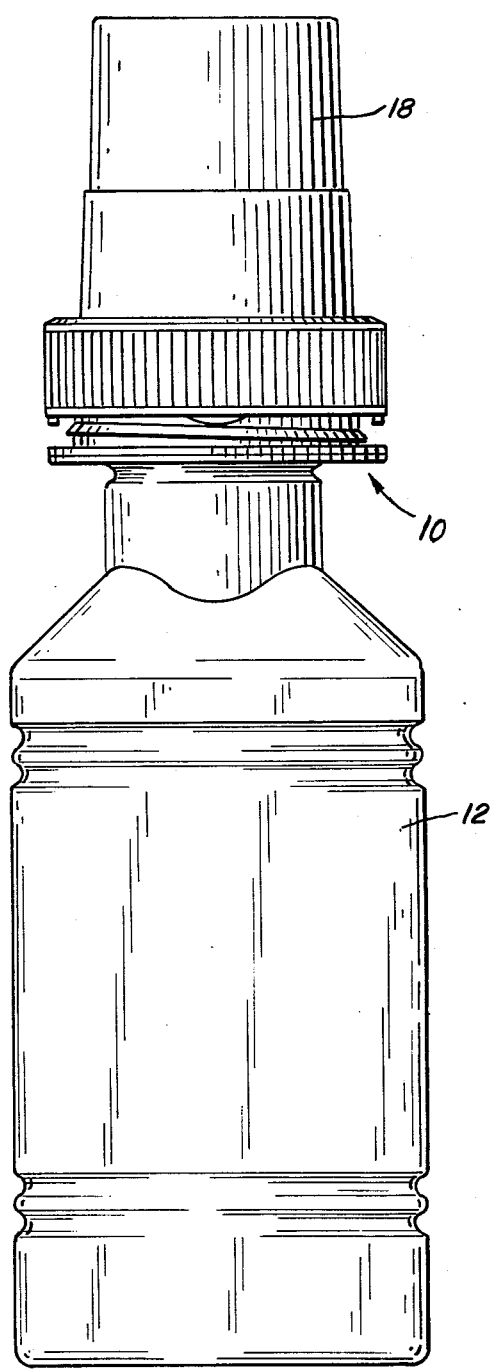
FIG. 1 is a front view of a gas humidifier set constructed in accordance with the principles of the present invention.
Figure 2:
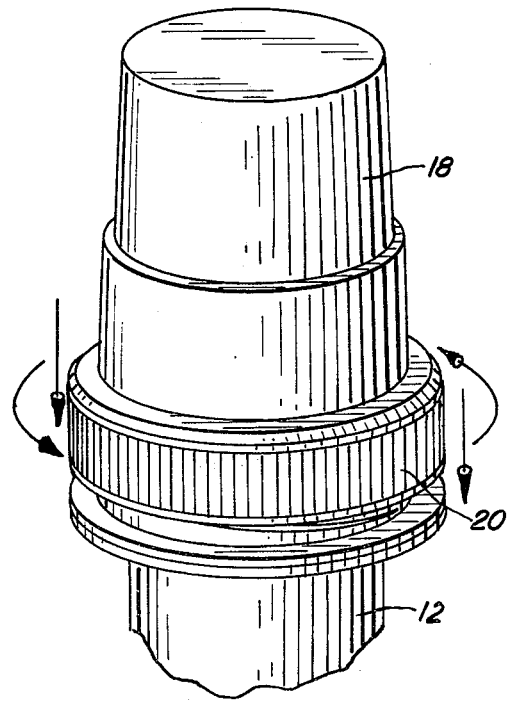
FIG. 2 is a fragmentary, perspective view of a form of covering cap which could be utilized with the gas humidifier set illustrated in FIG. 1.

Referring to the drawings, in FIG. 1 a gas humidifier set 10 is shown including a solution bottle 12. The solution bottle is preferably formed of a polyolefin plastic material and it contains a sterile water solution. A covering cap 18 is welded to the bottle and is utilized to maintain sterile the connector assembly that is covered by covering cap 18. Although the connector assembly is not shown in FIGS. 1 and 2, it is shown in detail in FIGS. 3–6, and it is described below.

Covering cap 18 may take various forms. In the illustrative embodiment, covering cap 18 comprises a cap molded of a polyolefin plastic material and having a driving cap 20. When driving cap 20 is manually turned forwardly (downwardly), cap 18 will become separated from the bottle 12, thereby displaying the connector assembly 22 (illustrated in FIG. 6). The construction and operation of the cap removal system is similar to that disclosed in U.S. Pat. No. 3,730,372 in which a container cover is separated by turning a cap forwardly (downwardly).

To understand the structure and operation of connector assembly 22, the structure of cap seal 24 (FIGS. 3 and 4) must first be explained. Cap seal 24 is formed of a polyolefin plastic material, is generally cup-shaped, and has at its top an outwardly extending annular flange 25, the bottom of which flange is welded to the top surface 26 of opening wall portion 16. Cap seal 24 carries a first upwardly extending tube 28 having a seal 30 at its lower extremity. A second tube 32 is provided, which extends upwardly with respect to a seal 34 and also downwardly with respect thereto, as shown most clearly in FIG. 3. An airway tube 36 is fastened to the bottom portion of tube 32, with the airway tube extending to the lower portion of the bottle. Airway tube 36 is coupled to the bottom portion of tube 32.

Figure 3:
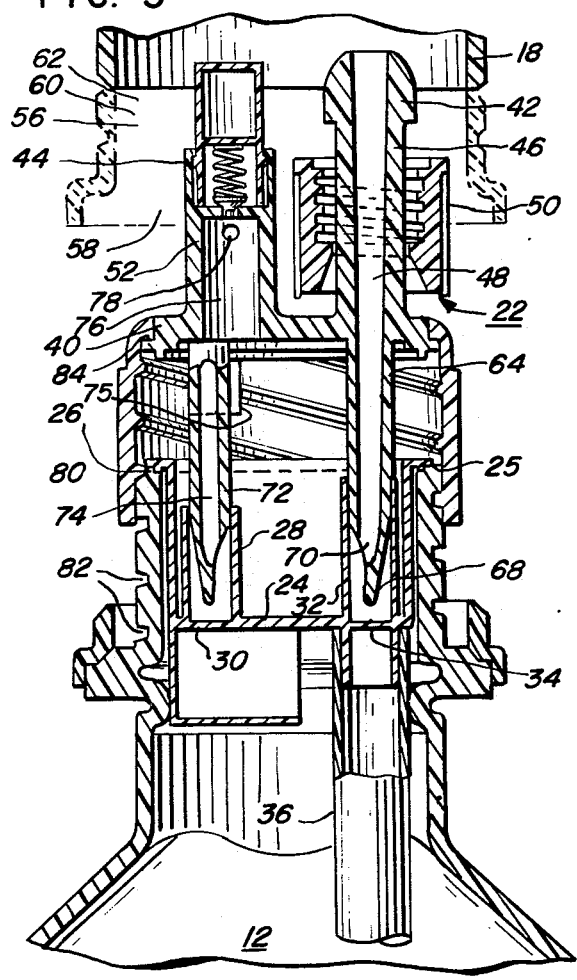
FIG. 3 is a cross-sectional view of a portion of the gas humidifier set of FIG. 1, showing the engagement of the connector assembly and solution bottle prior to use of the gas humidifier set.

Prior to use of the gas humidifier set and in its condition as shown in FIG. 3, the sterile water solution within bottle 12 is maintained sterile due to the sterile seal provided by cap seal 24. In order for there to be any communication between a gas supply and the solution within bottle 12, seals 30 and 34 must be pierced by connector assembly 22, as described below.

Connector assembly 22 comprises a generally disc-shaped member 40 which carries a gas inlet member 42 and a gas outlet member 44. Gas inlet member 42 includes an upper stem portion 46 having an axial bore 48, with stem portion 46 receiving an internally threaded member 50 for coupling the gas inlet member 42 to the flow meter coupled to the standard outlet of a gas supply. Gas outlet member 44 includes an upwardly extending stem portion 52 having an axial bore 76 and a lateral outlet coupling 54 having an axial bore 78 which communicates with axial bore 76.

Figure 7:
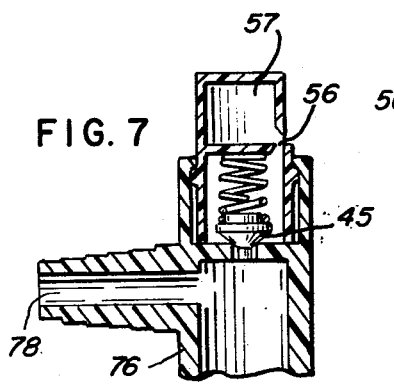
FIG. 7 is a cross-sectional elevation of the outlet member of the gas humidifier set of FIG. 1.
Figure 6:
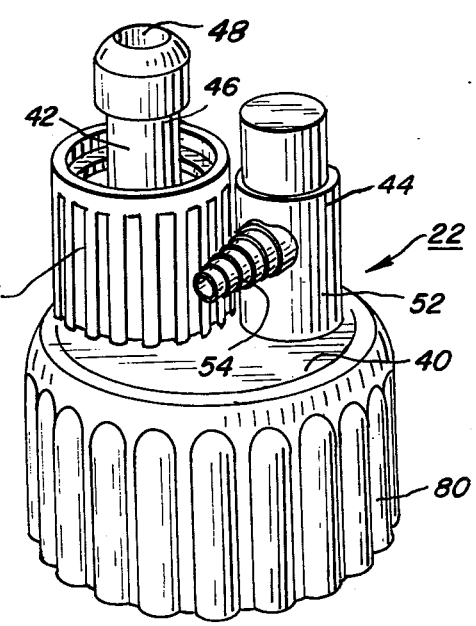
FIG. 6 is a perspective view of the connector assembly of the gas humidifier set of FIG. 1.

Referring to FIG. 7, it is seen that outlet member 44 includes a pressure relief valve 45, a vent 56, and a resonant cavity 57. When gas passage via bore 78 is insufficient, the gas pressure will force open valve 45 permitting venting through vent hole 56. A whistle will sound due to the resonant cavity 57, thereby signaling an operator.

Disc 40 also carries a downwardly extending tube 64 which is integrally formed therewith and also defines the lower portion of bore 48. The lower extremity 68 of tube 64 is pointed and bore 48 communicates with the outside.

Disc 40 also carries a downwardly extending spike 72 which is attached therewith and defines the lower portion of bore 74. The elements carried by disc 40 are so constructed that when the disc is lowered, tubes 64 and 72 will pierce seals 34 and 30, respectively, and gas flowing through inlet 42 via bore 48 will flow through aperture 70 and airway tube 36 into the solution within solution bottle 12. The humidified gas will flow into the space defined by cap seal 24 via bore 74, and through the gas outlet member via bores 76 and 78.

Figure 5:
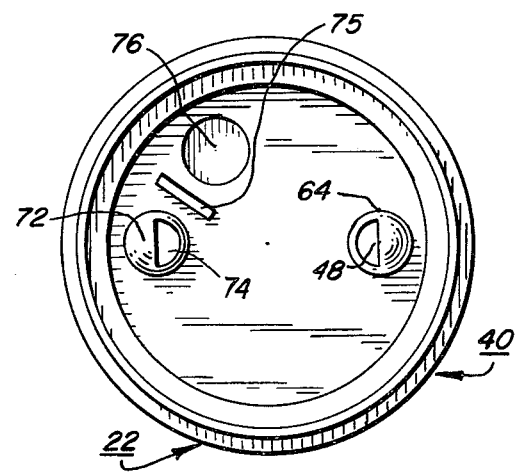
FIG. 5 is a bottom plan view of the disc-shaped member portion of the connector assembly of FIGS. 3 and 4.

Referring to FIG. 5, a downwardly extending flange, or baffle 75, is provided to block any direct line that particulate water might go up. This is useful because while it is the purpose for the humidified gas to flow upwardly via bore 74, on occasion, due to splashing or frothing in the bottle, water in particulate form will flow up the bore. Cap seal 24 and disk 40 form an expansion chamber. Gas flowing upwardly through bore 74 enters the chamber. As it enters the chamber, there is a rapid decrease in velocity and any large particles which might be suspended in the high velocity stream inside bore 74 will drop out and be held in cap 24. Because of the close proximity of bores 74 and 76, baffle 75 is provided to block any direct line that particulate water might go up.

Disc-shaped member 40 is operated by manually turning an annular manually-graspable member 80 having a downwardly extending circumferential side wall. Member 80 is internally threaded to cooperate with the external threads 82 of bottle 12. It is preferred that a four-start thread be utilized, as this allows use of a high pitch thread. In this manner, a fast thread is provided which enables tubes 64 and 72 to pierce seals 34 and 30 with only a small amount of turning. If only a single start thread is utilized, the high pitch thread platform is unstable and proper thread engagement may be difficult.

Figure 4:
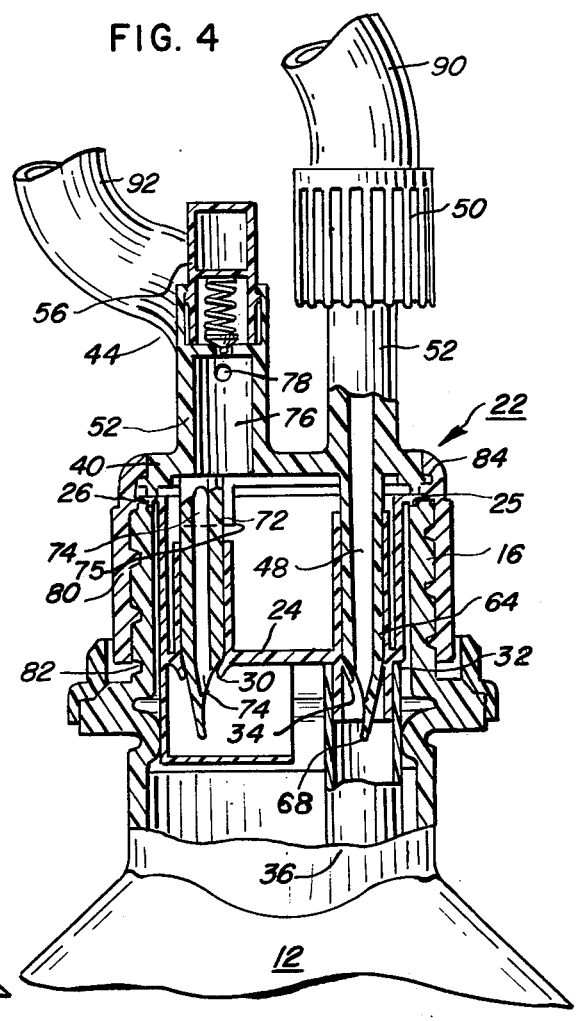
FIG. 4 is a cross-sectional view of a portion of the gas humidifier set of FIG. 1 during humidification.

Disc 40 is snap-fitted into annular member 80 with a bearing surface 84 (FIGS. 3 and 4) being provided so that disc 40 is rotatable with respect to annular member 80. Thus when annular member 80 is turned in a clockwise direction so that it screws downwardly over opening wall portion 16, disc 40 and its associated tubes 64 and 72 will be forced downwardly whereby the tubes will pierce seals 34 and 30, as shown in FIG. 4. In the FIG. 4 condition, the device is operating to feed gas from conduit 90 via gas inlet member 42, tube 64, opening 70 and airway tube 36 to the water solution within the bottle. Likewise, the humidified gas is fed via bore 74, bore 76 and bore 78 to outlet tube 92.

It can be seen that the gas humidifier set of the present invention is extremely simple to operate. The set is purchased in its condition shown in FIG. 1. When administration of oxygen to a patient is desired, driving cap 20 is turned forwardly to separate overcap 18 from bottle 12 and the cap 18 is removed. Coupling device 50 is screwed onto a conventional gas outlet tube 90 and a gas administration device having a tube 92 is fastened to outlet connector 54 with a friction fit. Annular member 80 is then turned in the clockwise direction, thereby forcing disc 40 and its associated tubes 72 and 64 downwardly to pierce seals 30 and 34, respectively.

After humidification of the gas is completed, the entire gas humidifier set 10 is discarded. It can be seen that a sterile, simple-to-operate and readily disposable system has been provided. It is preferable that the gas humidifier set 10 be formed of a polyolefin plastic material so that the entire assembly can be sterilized by autoclaving.

Although an illustrative embodiment of the invention has been shown and described, it is to be understood that various modifications and substitutions may be made by those skilled in the art without departing from the novel spirit and scope of the present invention.

What is claimed is:

1. A gas humidifier set comprising:
   a solution bottle;
   a cap-seal member overlying and sealing the mouth of said bottle, said cap-seal member defining spaced first and second piercable seal portions;
   first and second guide means extending upwardly from said cap-seal member, respectively adjacent to said first and second seal portions;
   a connector assembly enclosing a space between said cap-seal member, said connector assembly comprising:
   a gas inlet and outlet member defining a first conduit portion extending transversely through a base portion, an outer end of said first conduit portion being adapted for connection to a gas supply, and an inner end of said first conduit portion defining spike means and extending into said first cap-seal guide means in a position spaced from said cap-seal but adapted to puncture said first seal portion when moved into engagement therewith;
   a second conduit portion extending outwardly from and through said base portion of said gas inlet and outlet member, to define a gas passage through said base portion, the outer end of said second conduit portion being adapted for connection to a gas administration device;
   a third conduit portion extending downwardly from said base portion of said gas inlet and outlet member, said third conduit portion defining a gas passage communicating with the passage defined by said second conduit portion, the inner end of said third conduit portion defining spike means and extending into said second cap-seal guide means in a position spaced from said cap-seal but adapted to puncture said second cap-seal when moved into engagement therewith;

an annular member overlying said inlet and outlet member in sliding engagement therewith and engaging the neck of said solution bottle;

means associated with said connector assembly causing said first and second conduit portions to move in a direction to puncture said cap-seal when said annular member is moved in a selected direction;

said second and third conduit portions being axially spaced from each other, said space enclosed by said cap-seal member and base portion of the gas inlet member defining an expansion chamber for the passage of gas from said third conduit portion to said second conduit portion.

2. The gas humidifier set of claim 1 in which said base portion of the gas inlet and outlet member is in snap-fitted slidably-retained relation to said annular member, whereby said base portion, and said second and third conduit portions are positively held in said annular member, to hold said first and third conduit portions in spaced relation from said cap-seals until positively moved into rupturing engagement therewith by moving said annular member in the selected direction.

3. A gas humidifier set according to claim 1 wherein said solution bottle has a threaded neck, said annular member has internal threads engaging said neck and said inlet and outlet member is adapted to puncture said cap seal when said annular member is rotated in a selected direction.

4. A gas humidifier set according to claim 3 further comprising means to maintain the lower portion of said first tube portion spaced from said-cap seal while permitting said annular member to freely rotate until said annular member has been moved in its selected direction to puncture said cap-seal.

5. A gas humidifier set according to claim 1 further comprising baffle means at the lower surface of said base portion between said third tube portion and said second tube portion.

6. A gas humidifier set according to claim 1 wherein said first and second guide means are sleeve members extending upwardly from said cap seal and the lower portions of said first and third tube portions extend respectively, into said first and second guide means.

7. A gas humidifier set according to claim 6 further comprising an airway connected to the lower surface of said cap seal member at said first seal portion and extending to the lower portion of said bottle.

8. A gas humidifier set according to claim 7 further comprising a cap member overlying said cap seal member and said connector assembly, said cap member being in a normally sealed relationship to said bottle, and means for disengaging said cap member from said solution bottle to provide access to said connector assembly.

9. A gas humidifier set according to claim 8 wherein said gas humidifier set is formed of a polyolefin plastic material to permit sterilization by autoclaving.

10. A gas humidifier set according to claim 8 wherein said second tube portion has connected to it a pressure relief valve, a vent and a resonant cavity for providing an audible sound during venting.

* * * * *